United States Patent [19]

Biziere et al.

[11] Patent Number: 4,977,152
[45] Date of Patent: Dec. 11, 1990

[54] NOVEL TRICYCLIC DERIVATIVES WHICH ARE AGONISTS OF CHOLINERGIC RECEPTORS, AND DRUGS IN WHICH THEY ARE PRESENT

[75] Inventors: Kathleen Biziere, Clapiers; Camille G. Wermuth, Strasbourg; Paul Worms, Saint Gely Du Fesc; Jean-Jacques Bourguignon, Hipsheim, all of France

[73] Assignee: Societe Anonyme: Sanofi, Paris, France

[21] Appl. No.: 471,680

[22] Filed: Jan. 25, 1990

Related U.S. Application Data

[63] Continuation of Ser. No. 67,951, Jun. 30, 1987, abandoned.

[30] Foreign Application Priority Data

Jul. 3, 1986 [FR] France .................. 86 09681

[51] Int. Cl.$^5$ .................. A61K 31/535; A61K 31/50; C07D 237/36; C07D 413/12
[52] U.S. Cl. .................. 514/232.8; 514/248; 544/115; 544/234; 560/53
[58] Field of Search .................. 544/115, 234; 514/232.8, 248

[56] References Cited

U.S. PATENT DOCUMENTS 4,910,199  3/1990  Bourguignon et al. .......... 514/234.2

OTHER PUBLICATIONS

Lang et al., *Brain Research*, 267, pp. 271–280 (1983).
Christie et al., *Brit. J. Psychiat.* 138, pp. 46–50 (1981).
Harbaugh et al., *Neurosurgery*, 15, pp. 514–518 (1984).
Davies, *Brain Research*, 171, pp. 319–327 (1979).
Worms et al., *Psychopharmacology*, 93: 489–493 (1987).
Young et al., *Psychopharmacology*, 93: 494–497 (1987).
Perio et al., *Psychopharmacology*, 97: 262–268 (1989).
Worms et al., *Psychopharmacology*, 98: 286–288 (1989).
Kopelman, *Quarterly Journal of Experimental Psychology*, 38A, pp. 535–573 (1986).
Birdsall et al., *Atlas of Science: Pharmacology*, pp. 98–100 (1987).
Bartus et al., *Science*, vol. 217, pp. 408–417 (1982).
Davies et al., *Nature*, vol. 288, pp. 279–280 (1980).
Bartus, "Evidence for a Direct Cholinergic Involvement in the Scopolamine Induced Amnesia in Monkey", Pharmacol. Biochem. Behav. 9:833–836, 1978.
Bruno et al., Muscarinic Agonist Therapy of Alzheimer's Disease, A Clinical Trial of RS 86. Arc. Neurol. 43: 659–661, 1986.
Caine, Cholinomimetic Treatment Fails to Improve Memory Disorders, N. Engl. Med. 303: 585–586, 1980.
Chermet et al., Profils Psyshopharmacologiques de la Pilocarpine, de l'oxotremorine et de l'eserine, J. Pharmacol (Paris) 7: 227–240, 1976.
Christie et al., Physostigmine and Arecoline: Ettects of Intravenous Infusions in Alzheimer Persenile Dementia, Br. J. Psychiatry 138: 46–50, 1981.
Cummings et al., A Clinical Approach, Stoneham, Mass., Butterworths, 1983, pp. 36–56.
Enz et al., Pharmacological and Behavioural Effects of Pilocarpine, International Symposium on Muscarinic Cholinergic Mechanisms, Preund Publishing Houst Ltd. London, U.K. 1987, pp. 120–124.
Fisher et al., (Cis)—2—Methyl—Spiro—(1,3—Oxathiolane—5,3) Quinuclidine (AF 102B) A Novem Putative M1 Agonist as a Candidate Drug for the Treatment of Senile Dementia of Alzheimer's Type, International Symposium on Muscarinic Cholinergic Mechanism, Freund Publishing Houst Ltd. London, U.K. 1987, pp. 132–137.
Harbaugh et al., Preliminary Report, Intracranial Cholinergic Drug Infusion in Patients with Alzheimer's Disease, Neurosurgery, 15: 514–518, (1984).
Hollender et al., Cholinergic Approaches to the Treatment of Alzheimer's Disease, Br. Med. Bul. 42: 97–100, 1986.
Lang et al., Brain Muscarinic Receptors in Alzheimer's and Parkinson's Diseases, The Lancet, Nov. 25, 1989, p. 1279.
Metzler et al., Discriminative Stimulus Properties of Arecoline: A New Approach for Studying Central
(List continued on next page.)

*Primary Examiner*—Mukund J. Shah
*Assistant Examiner*—E. Bernhardt
*Attorney, Agent, or Firm*—Foley & Lardner, Schwartz, Jeffery, Schwaab, Mack, Blumenthal & Evans

[57] ABSTRACT

The invention relates to novel tricyclic derivatives which are agonists of cholinergic receptors and to drugs containing them.

These derivatives have the following formula:

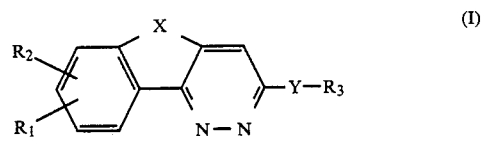

in which:
X represents a group $(CH_2)_n$, n representing an integer equal to 2, 3 or 4, or alternatively a vinylene group or a methylvinylene group;
$R_1$ and $R_2$, considered independently, represent hydrogen or a substituent occupying one of the free positions of the benzene ring and selected from the group comprising halogens, a lower alkyl group, a lower alkoxy group, a hydroxyl group, a thiol group, a nitro group and an optionally substituted amino group;
Y represents oxygen, sulfur or a group —NH—; and
$R_3$ is an amino group Application: agonists of the cholinergic receptors.

19 Claims, No Drawings

OTHER PUBLICATIONS

Muscarinic Receptors, Psychopharmacology, 75: 383–387, 1981.

Murray et al., Pilocarpine and Physostigmine Attenuate Spatial Memory Impairments Produced by Lesions of the Nucleus Basalis Magnocellularis, Behav. Neurosci, 100: 23–32, 1986.

Palacios et al., The Pharmacological Assessment of RS 86 (2—Ethyl—8—Methyl—2,8—Diazaspiro—4,5 Decan—1,3—Dion Hydrobromide) a Potent Specific Muscarinic Acetylcholine Receptor Agonist, Fur. J. Pharmacol., 125: 45–62, 1986.

Pradhan et al., Behavioural Effects of Arecoline in Rats, Psychopharmacology 17: 49–58, 1970.

Sitaram et al., Iluman Serial Learning: Enhancement with Arecholine and Choline and Impairment with Scopolamine, Science 201, 274–276, 1978.

Tariot et al., Multiple-Dose Arecoline Infusions in Alzheimer's Disease, Arch. Gen. Psychiatry, 45: 901–905, 1988.

Wettstein et al., Chlinical Trials with the Cholinergic Drugs RS 86 in Alzheimer's Disease (AD) and Senile Dementia of the Alzheimer Type (SDAT) Psychopharmacology, 84: 572–573, 1984.

Whitehouse et al., Alzheimer's Disease and Senile Dementia: Loss of Neurons in the Basal Forebrane, Science, 215: 1237–1239, 1982.

Birdsall et al., *Atlas of Science:* Pharmacology, pp. 98–100 (1987).

Shutske et al., *J. of Med. Chem.*, 31, p. 1278 (1988).

Family Health & Medical Guide, Consumer Guide Health Series, pp. 75–77 (1987).

Rodway et al., Chemical Abstracts, vol. 76, No. 14566v (1972).

TRYCYCLIC DERIVATIVES WHICH ARE AGONISTS OF CHOLINERGIC RECEPTORS, AND DRUGS IN WHICH THEY ARE PRESENT

This application is a continuation of application Ser. No. 07/067,951, filed June 30, 1987 now abandoned.

Senile dementia and in particular dementia of the Alzheimer type are serious complaints whose frequency is tending to increase with the increasing longevity of the population.

The studies undertaken by various authors have demonstrated, in Alzheimer's disease, the existence of a specific deficit of cortical cholinergic markers, causing serious disorders of the higher functions.

The results obtained using muscarinic agonists to treat senile dementia have proved encouraging. However, there are only a small number of muscarinic agonists in existence and they have been found difficult to manage in man.

Consequently, it is totally desirable at the present time to search for post-synaptic muscarinic agonists as a treatment for Alzheimer's disease.

The advantage of having selective central muscarinic agonists for correcting the cholinergic deficit in Alzheimer's disease has been mentioned especially in ISI Atlas of Science: Pharmacology (1987), p. 98 to 100.

It is to this problem that the present invention attempts to bring a solution in the form of novel products which act selectively on the $M_1$ central muscarinic receptors.

According to a first feature, the present invention relates to novel tricyclic compounds corresponding to the general formula:

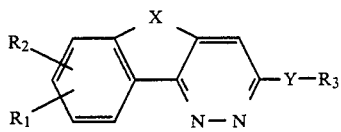

(I)

in which:
X represents a group $(CH_2)_n$, n representing an integer equal to 2, 3 or 4, or alternatively a vinylene group or a methylvinylene group;
$R_1$ and $R_2$, considered independently, represent hydrogen or a substituent occupying one of the free positions of the benzene ring and selected from the group comprising halogens, a lower alkyl group, a lower alkoxy group, a hydroxyl group, a thiol group, a nitro group and an optionally substituted amino group;
Y represents oxygen, sulfur or a group —NH—; and
$R_3$ represents:

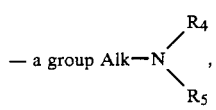

in which:
Alk represent a linear or branched alkylene group having from 2 to 5 carbon atoms; and
$R_4$ and $R_5$ each independently represent hydrogen, a lower alkyl group or a lower hydroxyalkyl group, or alternatively $R_4$ and $R_5$ form, with the nitrogen atom to which they are bonded, a 5-membered or 6-membered cyclic amino group optionally containing a second heteroatom and optionally substituted, and especially the pyrrolidin-1-yl, piperidino, morpholino, piperazin-1-yl or 2-oxomorpholino group;

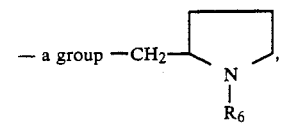

in which $R_6$ represents a lower alkyl group having 1 to 4 carbon atoms; or

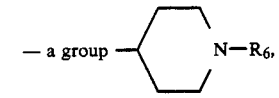

in which $R_6$ is as defined above; and their addition salts with pharmaceutically acceptable mineral or organic acids.

According to a second feature, the invention relates to a process for the preparation of the compounds of the formula (I), which can be represented by the following scheme:

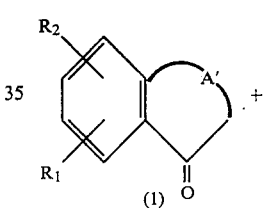

$$H-\underset{\underset{O}{\|}}{C}-COOR_7 \quad R_7 = H \text{ or } C_2H_5 \longrightarrow$$

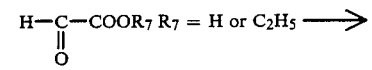

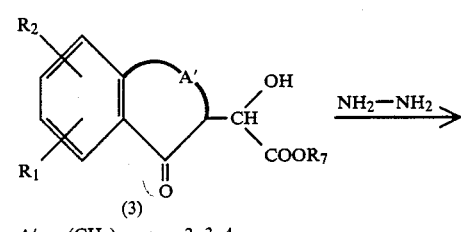

$A' = (CH_2)_n \quad n = 2, 3, 4$

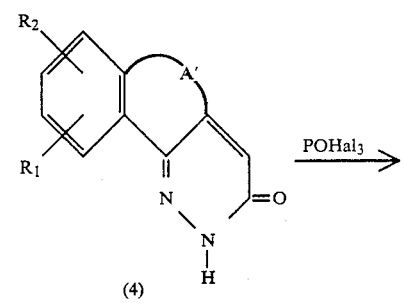

-continued

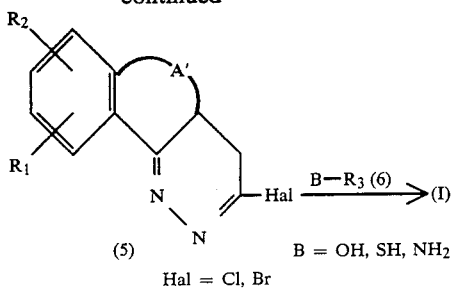

B = OH, SH, NH₂
Hal = Cl, Br

Reaction of ethyl glyoxylate or glyoxylic acid (2) with a benzocyclanone (1) at a temperature of between 60° and 150° C. gives the hydroxyester or hydroxyacid (3). This usually contains from 5 to 15% of the corresponding dehydration product (acrylic ester). It can be purified by chromatography or the crude product can be used directly for the next step.

The product (3) yields the pyridazone (4) on heating with hydrazine hydrate. The reaction is carried out either with a large excess of hydrazine hydrate or in a solvent selected from the group comprising hydroxylated solvents, especially n-butanol, or toluene.

In the majority of cases, the pyridazone (4) is obtained directly by reaction with hydrazine hydrate as indicated above.

In some cases, the 4-hydroxypyridazin-3-one formed as an intermediate is not dehydrated spontaneously in the reaction with hydrazine hydrate. In this case, it must be dehydrated by heating at 140° C. with a dehydrating agent such as polyphosphoric acid.

The pyridazone (4) yields the halogen derivative (5) when treated under reflux with an excess of phosphorus oxychloride or oxybromide.

Finally, the compound (1) is obtained by heating the halogen derivative (5) with the derivative (6) in a suitable solvent.

The solvent can be either a hydroxylated solvent such as n-butanol, or dimethylformamide; alternatively, it can consist of an excess of the derivative (6).

If the substitution reaction of the chlorine derivative is found to be slow, it can be facilitated by the addition of ammonium chloride if B is NH₂, or by the addition of sodium hydride if 8 represents OH or SH.

If appropriate, the resulting compounds (I) can be converted to salts by a known process.

If the compound (I) contains a substituent R₁ or R₂ which is capable of reacting during one or more steps of the synthesis, they must be blocked with the aid of a suitable reagent which will allow them to be regenerated at the end of the synthesis.

According to one variant of the process, the compounds (I) monosubstituted on the benzene nucleus, in the meta position relative to the direct bond between the benzene ring and the pyridazine ring, can be prepared from the chlorine derivative (5) (R₁=R₂=H) by nitration, leading to the corresponding nitro derivative (5) (R₁=NO₂, R₂=H).

This is converted to the corresponding compound (I) in the manner indicated above.

The resulting nitro derivatives (I) can be converted, by one or more known reactions, to compounds (I) in which R₁ represents a variety of substituents.

Thus, catalytic reduction gives the compounds (I) in which R₁=NH₂, R₂=H, and these can be used to form the compounds (I) in which R₁ is halogen, hydroxy etc. by diazotization followed by decomposition of the diazonium salt in the presence of suitable reagents.

Nitration and the reactions for converting the nitro group can also be performed on the chlorine derivative (5). These variously substituted chlorine derivatives lead to the corresponding compounds (I) as indicated above.

According to a second variant of the process, applicable to the compounds (I) in which Y is a sulfur atom, the pyridazone (4) can be converted to the thione (7) by reaction with phosphorus pentasulfide:

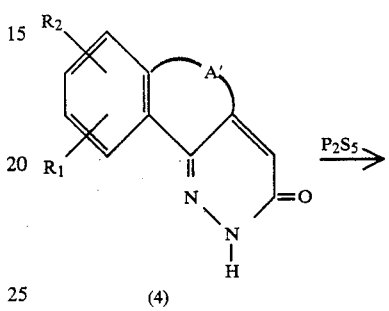

(4)

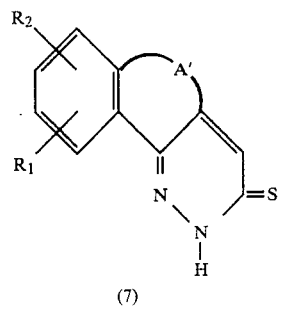

(7)

The reaction is carried out by heating the pyridazone at 80°-100° C. with an excess of phosphorus pentasulfide in the presence of sodium bicarbonate, in a suitable solvent such as acetonitrile, ethylene glycol dimethyl ether or a mixture of both, or alternatively pyridine, toluene or xylene.

The thione (7) is then substituted by reaction with a halide Hal-R₃, either in solution in an alcohol in the presence of the corresponding sodium alcoholate, or in dimethylformamide, to give the compound (I), which is purified by chromatography.

The compounds in which A' represents a vinylene group are obtained together with the compounds in which A' represents an ethylene group by heating the chlorine derivative (5) with an excess of the derivative (6) in the presence of ammonium chloride.

The 2 constituents of the resulting mixture are separated by chromatography.

The compounds (I) in which A' represents a methylvinylene group are obtained from the pyridazones (4) in which A' represents a methylethylene group. The reaction of phosphorus oxychloride with these pyridazones causes both the formation of the 3-chloropyridazine and the dehydrogenation of the methylethylene group to the methylvinylene group.

Finally, the compounds (I) in which R₃ represents a group:

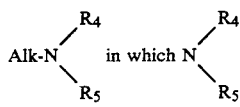

denotes a 2-oxomorpholino group can be prepared from the corresponding compounds (I) in which:

represents a group NHCH$_2$CH$_2$OH by substitution of the nitrogen by ethyl chloroacetate and cyclization of the resulting hydroxyester.

The starting cycloalkanones of the formula (1) are known or can be prepared by known processes, and especially by internal cyclization of the acids:

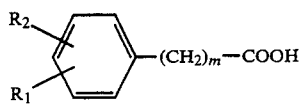
(8)

in which m is equal to n+1 in the presence of sulfuric acid or polyphosphoric acid. The acids (8) are themselves known or can be prepared by known processes, for example by reduction of the corresponding oxoacids:

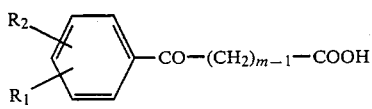

The examples which follow are given in order to illustrate the invention.

EXAMPLE 1

3-(2-Morpholinoethylamino)-6,7-dihydro-5H-benzocyclohepta[5,6-c]pyridazine dihydrochloride (SR 95639 A)

(I) X=(CH$_2$)$_3$; R$_1$=R$_2$=H: Y=NH:

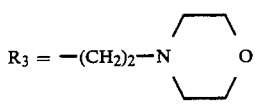

(A) Ethyl (5-oxo-6,7,8,9-tetrahydro-5H-benzocyclohepten-6-yl)glycolate

A mixture of 48 8 of 6,7,8,9-tetrahydro-5H-benzocyclohepten-5-one and 33.6 g of ethyl glyoxylate is heated at 135° C. for 24 hours. After cooling, the reaction mixture is purified by passage through a silica column. Elution with a cyclohexane/ethyl acetate mixture (95/5 vol/vol) gives the expected product in the form of a yellow oil.

Weight: 32 g; yield: 41%.

(B) 2,3,6,7-Tetrahydro-5H-benzocyclohepta[5,6-c]pyridazin-3-one

A solution of 15 g of the product obtained above in 250 ml of n-butanol is heated to the reflux temperature. 4.25 g of hydrazine hydrate are added dropwise to the solution and reflux is continued for 15 hours. The solvent is evaporated off in vacuo and the residue is recrystallized from 95° ethanol.

M.p.: 235° C.

(C) 3-Chloro-6,7-dihydro-5H-benzocyclohepta5,6-c]pyridazine

A mixture of 5 g of the pyridazone prepared above and 100 ml of phosphorus oxychloride is heated under reflux for 5 hours.

The reaction mixture is poured onto ice and rendered alkaline with a 20% aqueous solution of sodium hydroxide. The solid which separates out is filtered off, washed with water and dried in air. It is recrystallized from methanol.

M.p.: 159° C.

(D) SR 95639 A

A mixture of 4.6 g of the chlorine derivative-prepared above, 10.4 g of N-(2-aminoethyl)morpholine and 1.06 g of ammonium chloride is heated at 135° C. under argon for 6 hours.

The reaction mixture is poured into water and the solid which separates out is filtered off. It is recrystallized from 95° ethanol.

M.p.: 105° C.; weight: 4 g; yield: 62.5%.

Dihydrochloride 2.08 ml of concentrated hydrochloric acid are added to a solution of 4 g of the base in the minimum amount of hot isopropanol.

The dihydrochloride precipitates on the addition of ether. It is filtered off and recrystallized from 95° ethanol.

M.p.: 112°; weight: 5 g; yield: 91%.

Analysis for C$_{19}$H$_{24}$NO.2HCl.2.5H$_2$O (443.38)

|  | C | H | N |
| --- | --- | --- | --- |
| Calculated: | 51.46 | 7.05 | 12.64 |
| Found: | 51.65 | 7.23 | 12.78 |

EXAMPLES 2 to 8

The products of the formula (1) in which R$_1$=R$_2$=H, X=(CH$_2$)$_3$, Y=NH, collated in the table below, are obtained from the chlorine derivative of Example 1-C by following the procedure of Example 1-D but varying the amine derivative used.

In the case where the base does not crystallize, it is extracted with ethyl acetate and the salt is formed after evaporation of the solvent.

TABLE 1

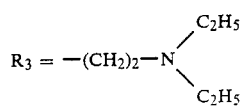

| Example no. | SR code no. | Alk | −N(R4)(R5) | Salt m.p.: °C. |
|---|---|---|---|---|
| 2 | 95640 A | (CH$_2$)$_2$ | −N(C$_2$H$_5$)(C$_2$H$_5$) | dihydrochloride 2.5H$_2$O 111° C. |
| 3 | 95817 A | (CH$_2$)$_3$ | −N⏀O (morpholino) | dihydrochloride 222° C. |
| 4 | 95818 A | (CH$_2$)$_3$ | −N(C$_2$H$_5$)(C$_2$H$_5$) | dihydrochloride 198° C. |
| 5 | 95819 A | (CH$_2$)$_2$ | −NH−CH(CH$_2$OH) | dihydrochloride 190° C. |
| 6 | 95824 A | (CH$_2$)$_2$ | −N(CH$_3$)(CH$_3$) | dihydrochloride 0.5H$_2$O 234–236° C. |
| 7 | 44694 A | (CH$_2$)$_2$ | −N⏀ (piperidino) | dihydrochloride 235–238° C. |
| 8 | 95883 A | (CH$_2$)$_2$ | −N⏀ (pyrrolidino) | dihydrochloride 137–139° C. |

EXAMPLE 9

9-Fluoro-3 (2-morpholinoethylamino)-6,7-dihydro-5H-benzocyclohepta[5,6-c]pyridazine dihydrochloride (SR 96108 A)

(I) X=(CH$_2$)$_3$; R$_1$=9-F: R$_2$=H: Y=NH:

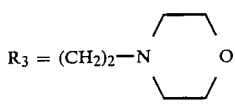

The procedure of Example 1 is followed using 2-fluoro-6,7,8,9-tetrahydro-5H-benzocyclohepten-5-one, prepared according to Journal of Organic Chemistry 1962, 27, 70–76, as the starting material.

The expected product is obtained in the same manner.
Base m.p.: 134° C.;
Dihydrochloride m.p.: 182°–183° C.

EXAMPLE 10

3-(2-Diethylaminoethylamino)-9,10-dimethyl-6,7-dihydro-5H-benzocyclohepta[5,6-c]pyridazine dihydrochloride (SR 44663 A)

(I) X=(CH$_2$)$_3$; R$_1$=9-CH$_3$; R$_2$=10-CH$_3$; Y=NH:

$$R_3 = -(CH_2)_2-N(C_2H_5)(C_2H_5)$$

(A) 9,10-Dimethyl-2,3,6,7-tetrahydro-5H-benzocyclohepta[5,6-c]pyridazin-3-one

A mixture of 27.15 g of 2,3-dimethyl-6,7,8,9-tetrahydro-5H-benzocyclohepten-5-one and 13.2 g of glyoxylic acid hydrate is heated at 75° C. for 15 hours. After cooling, the reaction mixture is taken up in water and methylene chloride and rendered alkaline by the addition of potassium carbonate.

The aqueous phase is separated off and extracted a second time with methylene chloride. The aqueous phase is cooled and acidified by the addition of concentrated hydrochloric acid. It is extracted 3 times with methylene chloride, the organic solution is dried and the solvent is then evaporated off to dryness. The product crystallizes and is used as such for the next step; weight: 24 g.

The product is dissolved in 140 ml of n-butanol and 7 ml of hydrazine hydrate are added. The reaction mixture is heated under reflux for 15 hours and then cooled to 4° C. The solid is filtered off and washed with a small amount of cold isopropanol and then with ether.

Weight: 13.5 g; m.p.: 270° C.

(B) 3-Chloro-9,10-dimethyl-6,7-dihydro-5H-benzocyclohepta5,6-c]pyridazine

A mixture of 5 g of the pyridazone obtained in (A) and 9.3 ml of phosphorus oxychloride in 26 ml of acetonitrile is heated under reflux for 4 hours.

The reaction mixture is poured into 400 ml of water and the pH is brought to 8 by the addition of concentrated aqueous ammonia. The crystals are filtered off, washed with water and dried.

Weight: 5.15 g; m.p.: 183°–4° C.

(C) SR 44663 A

A mixture of 5 g of the chlorine derivative obtained above and 12.5 ml of 2-diethylaminoethylamine in 100 ml of n-butanol is heated under reflux for 24 hours.

The solvent and the excess amine are removed by evaporation in vacuo and the residue is then taken up in methylene chloride. The solution is washed with water and then dried over magnesium sulfate.

After purification by chromatography on silica, the product crystallizes in the form of the base.

M.p.: 88°–9° C.

Dihydrochloride

The dihydrochloride is prepared by dissolving the base in the minimum amount of hot isopropanol and adding a solution of hydrochloric acid in ether. After drying in vacuo, 3.35 g of dihydrochloride are obtained.

M.p.: 140°–145° C., hygroscopic.

EXAMPLE 11

9,10-Dichloro-3-(2-diethylaminoethylamino)-6,7-dihydro-5H-benzocyclohepta[5,6-c]pyridazine dihydrochloride (SR 44695 A)

(I) $X=(CH_2)_3$; $R_1=9\text{-}Cl$; $R_2=10\text{-}Cl$: $Y=NH$

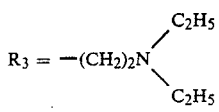

The compounds below are obtained successively from 2,3-dichloro-6,7,8,9-tetrahydro-5H-benzocyclohepten-5-one by following the procedure of Example 10:

9,10-dichloro-2,3,6,7-tetrahydro-5H-benzocyclohepta[5,6-c]pyridazin-3-one, m.p. >250° C.;

3,9,10-trichloro-6,7-dihydro-5H-benzocyclohepta5,6-c]pyridazine, m.p.: 185°–186° C.; and SR 44695 A: base m.p.: 100°–101° C.; dihydrochloride m.p.: 100°–105° C.

EXAMPLES 12 to 16

The compounds of the formula (I) collated in Table 2 are obtained from the 3-chloro derivatives of Examples 10 and 11 by following the procedure of Example 10 but varying the amine used.

TABLE 2

| Example no. | SR code no. | $R_1$ | $R_2$ | $-N\diagdown^{R_4}_{R_5}$ | Salt or base m.p.: °C. |
|---|---|---|---|---|---|
| 12 | 44650 A | $CH_3$ | $CH_3$ | 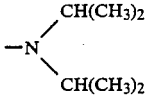 | dihydrochloride 140–144° C. (hygroscopic) |
| 13 | 44664 A | $CH_3$ | $CH_3$ | $-N\diagdown^{CH(CH_3)_2}_{CH(CH_3)_2}$ | base 128–129° C. |
| 14 | 44696 A | Cl | Cl | $-N\diagdown^{CH_3}_{CH_3}$ | base 102–103° C. |
| 15 | 44705 A | Cl | Cl |  | base 177–179° C. |
| 16 | 44706 A | $CH_3$ | $CH_3$ | $-N\diagdown^{(CH_2)_3CH_3}_{(CH_2)_3CH_3}$ | dihydrochloride 156–160° C. |

EXAMPLE 17

3-[(1-Ethylpyrrolidin-2-yl)methylamino]-6,7-dihydro-5H-benzocyclohepta-5,6-c]pyridazine dihydrochloride (SR 95879 A)

(I) $X=(CH_2)_3$; $R_1=R_2=H$: $Y=NH$:

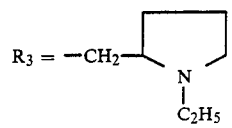

The procedure of Example 1D) is followed starting from the chlorine derivative of Example 1C) and 2-aminomethyl-1-ethylpyrrolidine.

The expected product, isolated in the form of the dihydrochloride, is obtained in the same manner.

M.p.: 158° C.

EXAMPLE 18

3-(1-Methylpiperidin-4-yl)amino]-6,7-dihydro-5H-benzocyclohepta[5,6-c]pyridazine dihydrochloride (SR 96093 A)

The procedure of Example (1D) is followed starting from the chlorine derivative obtained in Example (1C) and 4-amino-1-methylpiperidine.

The expected product, isolated in the form of the dihydrochloride, is obtained in the same manner.

M.p.: 255° C.

EXAMPLE 19

10,11-Dimethyl-3-(2-piperidinoethylamino)-5,6,7,8-tetrahydrobenzocycloocta[5,6-c]pyridazine dihydrochloride (SR 44704 A)

(I) $X=(CH_2)_4$; $R_1=10\text{-}CH_3$; $R_2=11\text{-}CH_3$; $Y=NH$;

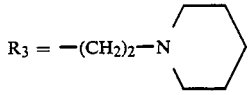

(A) 10,11-Dimethyl-2,3,5,6,7,8-hexahydrobenzocycloocta[5, 6-c]pyridazin-3-one

A mixture of 13 g of 2,3-dimethyl-5,6,7,8,9,10-hexahydrobenzocycloocten-5-one and 5.85 g of glyoxylic acid monohydrate is heated at 80° C. for 15 hours.

It is treated as indicated in Example 10-A to give 17.5 g of solid product. This solid is taken up in 70 ml of n-butanol and 5 ml of hydrazine hydrate are added. The mixture is heated under reflux for 15 hours and cooled. The solid which has separated out is filtered off.

The NMR spectrum shows that the product is the 4-hydroxy compound which has not been dehydrated. The solid is therefore taken up in polyphosphoric acid (12 ml per gram of product) and heated at 140° C. The progress of the reaction is followed by TLC (eluent: $CH_2Cl_2$/MeOH, 95/5 vol/vol). When the hydroxy compound has entirely disappeared, the reaction mixture is poured into iced water. The solid is filtered off, washed with water and dried in an oven in vacuo.

(B) 3-Chloro-10,11-dimethyl-5,6,7,8-tetrahydrobenzocycloocta[5,6-c]pyridazine

The procedure of Example 10 (B) is followed starting from the product obtained above.

M.p.: 132°–134° C.

(C) SR 44704 A

A mixture of 4.5 g of the chlorine derivative obtained above and 12.5 ml of 2-piperidinoethylamine in 75 ml of n-butanol is heated under reflux for 48 hours.

The solvent is evaporated off in vacuo and the residue is taken up in ethyl acetate. The solution is washed with water and dried over magnesium sulfate.

The product is purified on a column of silica. Elution with a methylene chloride/methanol/aqueous ammonia mixture (80/20/1 vol/vol) gives the expected product.
M.p.: 115° C.

Dihydrochloride

The base is dissolved in ether and the hydrochloride is precipitated with hydrochloric acid.
M.p.: 215° C.

EXAMPLE 20

3-(2-Diethylaminoethylamino)-10,11-dimethyl-5,6,7,8-tetrahydrobenzocycloocta[5,6-c]pyridazine dihydrochloride (SR 44703 A)

The procedure of Example 19 (C) is followed starting from the chlorine derivative of Example 19 (B) and 2-diethylaminoethylamine.

The dihydrochloride is obtained in the same manner.
M p.: 85°–88° C.

EXAMPLE 21

3-(2-Diethylaminoethylamino)-10-nitro-6,7-dihydro-5H-benzocyclohepta[5,6-c]pyridazine dihydrochloride (SR 95777 A)

(I) $X=(CH_2)_3$; $R=10$-$NO_2$; $R_2=H$; $Y=NH$;

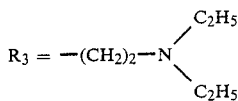

(A) 3-Chloro-10-nitro-6,7-dihydro-5H-benzocyclohepta5,6-c]pyridazine

A solution of 3.85 g of potassium nitrate in 50 ml of concentrated sulfuric acid is added slowly, over a period of about 15 minutes, to a solution of 8 g of 3-chloro-6,7-dihydro-5H-benzocyclohepta5,6-c]pyridazine (Example 1-C) in 70 ml of concentrated sulfuric acid.

The reaction mixture is poured into 300 ml of iced water and the precipitate formed is filtered off.

It is rinsed with copious amounts of water and then dried.

It is chromatographed on a column of silica. Elution with a hexane/ethyl acetate mixture (3/1 vol/vol) gives the expected product.

M.p.: 174° C.; weight: 5.4 g; yield: 57%.

Continued elution gives a small amount of a mononitro derivative identified as the corresponding 8-nitro compound.

(B) SR 95777 A

A mixture of 3.88 g of the nitro derivative obtained above and 5.08 g of 2-diethylaminoethylamine in 150 ml of n-butanol is heated under reflux for 17 hours.

The n-butanol is evaporated off in vacuo and the residue is chromatographed on a column of silica.

The expected product is obtained by elution with an ethyl acetate/hexane/aqueous ammonia mixture (89/10/1 vol/vol), after the elimination of impurities in the first runnings.

Weight: 2.57 g; yield: 50%.

Dihydrochloride

The base obtained above is dissolved in hot isopropanol and an excess of concentrated hydrochloric acid is added. The dihydrochloride is left to crystallize and it is then filtered off, rinsed with isopropyl ether and recrystallized from an isopropanol/ethyl ether mixture.

This gives 2.6 g of dihydrochloride.
M.p.: 198°–200° C.

EXAMPLE 22

3-(2-Morpholinoethylamino)-8-nitro-6,7-dihydro-5H-benzocyclohepta[5,6-c]pyridazine dihydrochloride (SR 96100 A)

(I) $X=(CH_2)_3$; $R_1=8$-$NO_2$; $R_2=H$; $Y=NH$;

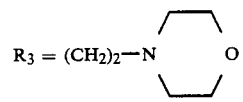

The procedure of Example 21 (B) is followed starting from the 8-nitro chlorine derivative obtained in Example 21 (A) and 2-morpholinoethylamine. The expected product, isolated as the dihydrochloride, is obtained in the same manner.

M.p. : 206°–207° C.

EXAMPLES 23 and 24

The compounds (I) in Table 3 are obtained by following the procedure of Example 21 but varying the amine derivative used in step B).

TABLE 3

| Example no. | SR code no. | Alk | R4 / R5 | Base or salt m.p.: °C. |
|---|---|---|---|---|
| 23 | 44681 A | $(CH_2)_2$ | —N(CH₃)(CH₃) | dihydrochloride 0.5H₂O 227–229° C. |
| 24 | 44697 A | $(CH_2)_2$ | —N(CH—(CH₃)₂)(CH—(CH₃)₂) | base 124–127° C. |

EXAMPLE 25

10-Amino-3-(Z-diethylaminoethylamino)-6,7-dihydro-5H-benzocyclohepta[5,6-c]pyridazine dihydrochloride (SR 95776 A)

(I) $X=(CH_2)_3$; $R_1=10$-$NH_2$; $R_2=H$; $Y=NH$;

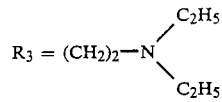

0.1 g of 5% palladium-on-charcoal is added to a solution of 1.3 g of the nitro compound of Example 21 in 50 ml of methanol and hydrogenation is carried out at ordinary temperature and pressure for 3 hours.

The catalyst is filtered off and the solvent is evaporated off. The residue is recrystallized from an isopropanol/anhydrous ether mixture.

The expected product is obtained.

M.p.: 182° C.; weight: 0.77 g; yield: 60%.

EXAMPLE 26

3-Z-(2-Oxomorpholino)ethylamino]-6,7-dihydro-5H-benzocyclohepta[5,6-c]pyridazine hydrochloride (SR 95696 A)

(I) $X=(CH_2)_3$ $R_1=R_2=H$; $Y=NH$;

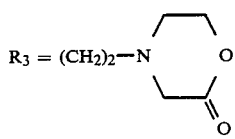

A solution of sodium methylate prepared from 0.23 g of sodium and 25 ml of methanol is added to a solution of 2 g of 3-[2-(2-hydroxyethylamino)ethylamino]-6,7-dihydro-5H-benzocyclohepta[5,6-c]pyridazine (Example 5) in 35 ml of methanol. After stirring for one hour at room temperature, 0.8 ml of ethyl chloroacetate is added and stirring is continued at room temperature, under an argon atmosphere, for 15 hours.

The methanol is evaporated off and the residue is taken up in a saturated aqueous solution of sodium chloride.

Extraction is carried out with ethyl acetate and the organic solution is dried and evaporated to dryness in vacuo.

The oily residue is purified by chromatography on a column of silica. Elution with an ethyl acetate/methanol mixture (8/2 vol/vol) gives 1.7 g of the expected product.

Yield: 74%.

Hydrochloride

The above base is dissolved in methanol and a stream of hydrogen chloride gas is bubbled into the solution. The reaction mixture is evaporated to dryness and the residue is redissolved in the minimum amount of methanol. The hydrochloride precipitates on the addition of anhydrous ether. It is filtered off and recrystallized from a 95° ethanol/ether mixture.

M p.: 211° C.

Analysis for $C_{19}H_{22}N_4O_2.HCl$ (374.86)

| | | | |
|---|---|---|---|
| Calculated | C: 60.87 | H: 6.18 | N: 14.95 |
| Found | 60.71 | 6.20 | 15.03 |

EXAMPLE 27

3-(3-Diethylaminopropylamino)-5,6-dihydrobenzo[h]-cinnoline dihydrochloride (SR 95746 A)

(I) $X=(CH_2)_2$; $R_1=R_2=H$: $Y=NH$:

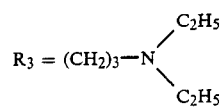

(A) Ethyl (1-oxo-1,2,3,4-tetrahydronaphth-2-yl)glycolate

The procedure of Example 1-A is followed using α-tetralone as the starting ketone.

The expected product is obtained in the form of an oil by chromatography on a column of silica using a hexane/ethyl acetate mixture (60/40 vol/vol) as the eluent.

Yield: 63%.

(B) 2,3,5,6-Tetrahydrobenzo[h]cinnolin-3-one

The procedure of Example 1-B is followed starting from the product obtained above.

The expected product crystallizes on cooling the reaction mixture to 0° C. It is filtered off and washed with isopropyl ether.

M.p.: 236° C.

(C) 3-Chloro-5,6-dihydrobenzo[h]cinnoline

The chlorinated product is obtained from the product prepared above by following the procedure of Example 1-C.

M.p.: 154° C.: yield: 60%.

(D) SR 95746 A

A mixture of 2.16 g of the chlorine derivative obtained above and 3.9 g of 3-diethylaminopropylamine in 100 ml of n-butanol is heated under reflux for 24 hours. The solvent is evaporated off to dryness in vacuo and the residue is taken up in ethyl acetate. The mixture is extracted with a dilute aqueous solution of hydrochloric acid and the aqueous phase is separated off and rendered alkaline with potassium carbonate. Extraction is carried out with ethyl acetate and the solution is washed with water. The solution is dried over sodium sulfate and the solvent is then evaporated off to dryness in vacuo. The residue is purified by chromatography on a column of silica.

Elution with an ethyl acetate/methanol/aqueous ammonia mixture (85/10/5 vol/vol) gives an oil.

Weight: 0.55 g.

Dihydrochloride 0.5 g of the base is dissolved in isopropanol and 0.27 ml of concentrated hydrochloric acid is added.

The hydrochloride crystallizes. It is filtered off and washed with ether. It is recrystallized twice from isopropanol to give the dihydrochloride.

M.p.: 140° C.; yield: 65%.

Analysis with $1.25H_2O$

| | | | |
|---|---|---|---|
| Calculated | C: 56.21 | H: 7.57 | N: 13.80 |
| Found | 56.26 | 8.08 | 13.70 |

EXAMPLE 28

3-(2-Morpholinoethylamino)-5,6-dihydrobenzo[h]cinnoline dihydrochloride (SR 95695 A)

(I) $X=(CH_2)_2$; $R_1=R_2=H$; $Y=NH$;

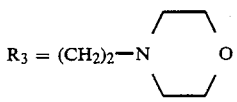

The procedure of Example 27 (D) is followed, the 3-diethylaminopropylamine being replaced by an equivalent amount of 2-morpholinoethylamine. The expected product, in the form of the di-hydrochloride, is obtained in the same manner.

M.p.: 224° C. (95° ethanol).

The salt crystallizes with 2 molecules of water. Analysis for $C_{18}H_{22}N_4O.2HCl.2H_2O$ (419.33)

| | C: 51.55 | H: 6.72 | N: 13.36 |
|---|---|---|---|
| Calculated | | | |
| Found | 51.66 | 6.55 | 13.10 |

EXAMPLE 29

3-(2-Diethylaminoethylamino)-5,6-dihydrobenzo[h]cinnoline dihydrochloride (SR 96054)

(I) $X=(CH_2)_2$; $R_1=R_2=H$; $Y=NH$:

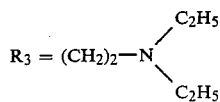

The procedure of Example 27 is followed and the expected product, isolated as the dihydrochloride, is obtained in the same manner.

M.p.: 177°-178° C.

EXAMPLE 30

3-(2-Morpholinoethylamino)benzo[h]cinnoline dihydrochloride (SR 95679 A)

(I) $X=-CH=CH-$: $R_1=R_232$ H: $Y=NH$:

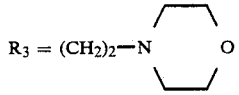

A mixture of 1.25 g of the chlorine derivative obtained in Example 27 (C), 3 g of 2-morpholinoethylamine and 0.3 g of ammonium chloride is heated at 135° C. under argon for 6 hours.

The reaction mixture is poured into water and extracted with ethyl acetate. The organic phase is extracted with 2 N sulfuric acid and the aqueous phase is separated off. The latter is rendered alkaline with sodium carbonate and extracted with ethyl acetate. The solution is dried.

It contains 2 constituents, which are separated by chromatography on a column of silica using an ethyl acetate/methanol mixture (95/5 vol/vol) as the eluent.

The title product, weighing 0.400 g, is obtained first; continued elution then makes it possible to isolate 0.300 g of the corresponding dihydrogenated product, which is identical in every respect to the product described in Example 28.

Dihydrochloride

The 0.400 g of base is dissolved in hot isopropanol and 0.22 ml of concentrated hydrochloric acid is added. The hydrochloride precipitates on cooling. It is filtered off and recrystallized from 95° ethanol.

M.p.: 210° C. (decomposition), yellow solid. Analysis with 1.5 molecules of water for $C_{18}H_{20}N_4O.2HCl.1.5H_2O$ (408.22)

| | C: 52.94 | H: 6.17 | N: 13.72 |
|---|---|---|---|
| Calculated | | | |
| Found | 52.95 | 6.32 | 13.51 |

EXAMPLE 31

3-(2-Diethylaminoethylamino)benzo[h]cinnoline dihydrochloride (SR 96055 A)

(I) $X=CH'CH$; $R_1=R_2=H$; $Y=NH$:

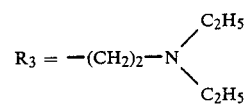

The procedure of Example 30 is followed, the 2-morpholinoethylamine being replaced by an equivalent amount of 2-diethylaminoethylamine. The expected product is isolated in the same manner.

Base m.p.: 90° C.

Dihydrochloride m.p.: 137°-138° C. (crystallized with one molecule of water).

EXAMPLE 32

5-3-(2-morpholinoethylamino)benzo[h]cinnoline dihydrochloride (SR 96057 A)

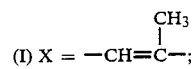

$R_1=R_2=H$; $Y=NH$;

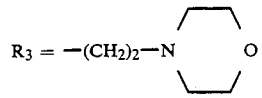

(A) 5-Methyl-2,3,5,6-tetrahydrobenzo[h]cinnolin-3-one

The procedure of Example 27, sections A and B, is followed starting from 3-methyl-3,4-dihydro-2H-naphthalen-1-one.

M.p.: 218° C.

(B) 3-Chloro-5-methylbenzo[h]cinnoline 7.6 g of the cinnolinone prepared above and 50 ml of phosphorus oxychloride are heated at 80° C. for 4 hours.

The mixture is poured onto crushed ice and extracted with ethyl acetate. The organic solution is washed with water and dried cover- sodium sulfate and the solvent is evaporated off to dryness.

The mixture is purified by chromatography on a column of silica.

Elution with an ethyl acetate/hexane mixture (50/50 vol/vol) gives the product in the form of pale yellow crystals.

(C) SR 96057 A

The procedure of Example 1 (D) is followed starting from the chlorine derivative obtained above and 2-morpholinoethylamine.

The expected product, isolated in the form of the dihydrochloride, is obtained in the same manner.
M.p.: 176°–177° C.

EXAMPLE 33

10-Chloro-3-(2-diethylaminoethylamino)-6,7-dihydro-5H-benzocyclohepta[5,6-c]pyridazine dihydrochloride (SR 95878 A)

(I) $X=(CH_2)_3$ $R_1=$ 10-Clm $R_2=H$: $Y=NH$;

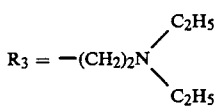

(A) 10-Amino-3-chloro-6,7-dihydro-5H-benzocyclohepta[5, 6-c]pyridazine 8 ml of acetic acid are added to a mixture of 2.75 g of 3-chloro-10-nitro-6,7-dihydro-5H-benzocyclohepta[5,6-c]pyridazine (Example 21A) and 2 g of iron powder in 100 ml of ethanol and the reaction mixture is heated under reflux for 4 hours. It is then left for 15 hours at 20° C. and filtered on Celite. The alcohol is evaporated off and the residue is taken up with water and methylene chloride.

The aqueous phase is separated off and rendered alkaline with sodium hydroxide. It is extracted twice with methylene chloride and the organic solution is dried over sodium sulfate. The solvent is evaporated off in vacuo.

This gives a yellow solid (1.6 g).
M.p.: 171°–172° C.

(B) 3,10-Dichloro-6,7-dihydro-5H-benzocyclohepta5,6-c-pyridazine 4.5 g of the amine derivative obtained above are dissolved in 22 ml of water and 5 ml of concentrated hydrochloric acid. The solution is cooled to 0° C. and an acidic aqueous solution of sodium nitrite (1.4 g) is added rapidly, the temperature of the mixture being kept below 7° C.

The reaction mixture is stirred for 15 minutes and added rapidly to a solution of 2.25 g of cuprous chloride in 30 ml of water acidified with hydrochloric acid.

The mixture is stirred for 2 hours at room temperature and the precipitate formed is filtered off and washed with water. It is redissolved in methylene chloride and washed with water. The organic solution is dried over sodium sulfate and the solvent is evaporated off to dryness.

This gives 4.3 g of the expected product
M.p.: 115° C.

(C) SR 95878 A

The procedure of Example 1 (D) is followed starting from the chlorine derivative obtained above.

The expected product, isolated in the form of the dihydrochloride, is obtained in the same manner. M.p.: 188° C. (crystallized with one molecule of water).

EXAMPLE 34

3-(2-Dimethylaminoethoxy)-5,6-dihydrobenzo[h]cinnoline hydrochloride (SR 95745 A)

(I) $X=(CH_2)_2$, $R_1=R_2=H$; $Y=O$:

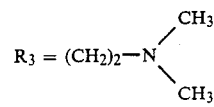

A mixture of 5.84 g of 2-dimethylaminoethanol and 0.5 g of sodium hydride is heated to 80° C. under a nitrogen atmosphere. After cooling to room temperature, 2.16 g of the chlorine derivative obtained in Example 27C) are added and the reaction mixture is heated again at 80° C. for 1 hour 30 minutes. After cooling, it is diluted with ethyl acetate and the organic solution is washed with water and then extracted with a dilute aqueous solution of hydrochloric acid. The aqueous phase is separated off, rendered alkaline with potassium carbonate and extracted with ethyl acetate. The organic phase is washed with water and dried over sodium sulfate and the solvent is evaporated off to dryness.

The residue is purified by chromatography on a column of silica. Elution with an ethyl acetate/methanol/aqueous ammonia mixture (85/10/5 vol/vol) gives an orange oil (2 g).

Yield: 67%.

Hydrochloride 2 g of the base are dissolved in isopropanol and 0.57 ml of concentrated hydrochloric acid is added. The hydrochloride precipitates on the addition of ether. It is filtered off and recrystallized from an isopropanol/ether mixture.

This gives 1.45 g of the expected product.
M.p.: 179° C.: yield: 65%. Analysis for $C_{18}H_{23}N_3O \cdot HCl$ (333.84)

| | | | |
|---|---|---|---|
| Calculated | C: 64.75 | H: 7.24 | N: 12.58 |
| Found | 64.39 | 7.40 | 12.45 |

EXAMPLE 35

3-(2-Dimethylaminoethoxy)-6,7-dihydro-5H-benzocyclohepta[5,6-c]pyridazine hydrochloride (SR 95822 A)

The procedure of Example 34 is followed starting from the chlorine derivative of Example 1 (C). The expected hydrochloride is isolated in the same manner
M p.: 182° C.
Analysis for $C_{19}H_{25}N_3O \cdot HCl$ (347.87)

| | | | |
|---|---|---|---|
| Calculated | C: 65.59 | H: 7.53 | N: 12.07 |
| Found | 65.72 | 7.81 | 11.96 |

EXAMPLE 36

3-(2-Diethylaminoethylthio)-5,6-dihydrobenzo[h]cinnoline hydrochloride (SR 95743 A)

(I) $X=(CH_2)_2$; $R_1=R_2=H$; $Y=S$:

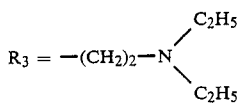

(A) 2,3,5,6-Tetrahydrobenzo[h]cinnoline-3-thione 5.34 g of 2,3,5,6-tetrahydrobenzoh]cinnolin-3-one (Example 27B)) are dissolved in 27 ml of acetonitrile and 27 ml of ethylene glycol dimethyl ether. 16.2 g of phosphorus pentasulfide are then added, after which 4.2 g of sodium bicarbonate are added in small portions at room temperature, with efficient stirring.

The mixture is subsequently heated for 4 hours at 90° C., the solvents are then evaporated off in vacuo and the residue is then poured into water. The crystals are filtered off and dried.

This gives 5 g of the expected product.
M.p.: 236°–240° C.; yield: 85%.

(B) SR 95743 A 3 g of the above thione are dissolved in an ethanolic solution of sodium ethylate obtained from 0.7 g of sodium. 2.58 g of 2-diethylamino-1-chloroethane hydrochloride are added, with stirring, and the mixture is left for 15 hours at room temperature. The solvent is evaporated off to dryness in vacuo and the residue is taken up in ethyl acetate. The organic solution is washed with water and then extracted with dilute hydrochloric acid. The aqueous phase is separated off and rendered alkaline with potassium carbonate. It is extracted with ethyl acetate and the extract is washed with water and dried over sodium sulfate. The solvent is evaporated off to dryness to give a brown oil (2.45 g), which is purified by chromatography on a column of silica. The expected product (1.6 g) is obtained by elution with an ethyl acetate/methanol mixture (90/10 vol/vol), after the elimination of impurities in the first runnings.

Hydrochloride 0.14 ml of concentrated hydrochloric acid is added to a solution of 0.5 g of the base in isopropanol and the hydrochloride is then precipitated by the addition of ether. The crystals are filtered off and recrystallized from absolute ethanol.

This gives 0.4 g of the expected product.
M.p.: 228° C.
Analysis for $C_{18}H_{23}N_3S.HCl$ (349.90)

| | C: 61.17 | H: 6.91 | N: 12.00 |
|---|---|---|---|
| Calculated | | | |
| Found | 61.36 | 6.89 | 11.88 |

EXAMPLE 37

3-(2-Diethylaminoethylthio)-6,7-dihydro-5H-benzocyclohepta[5,6-c]pyridazine hydrochloride (SR 95820 A)

(1) $X=(CH_2)_3$ $R_1=R_2=H$; $Y=S$:

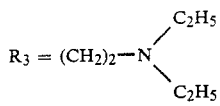

The procedure of Example 36 is followed starting from the pyridazinone of Example 1-B. The expected product is obtained in the same manner.
M.p.: 174° C.
Analysis for $C_{19}H_{25}N_3S.HCl$ (363.93)

| | C: 62.70 | H: 7.20 | N: 11.54 |
|---|---|---|---|
| Calculated | | | |
| Found | 62.53 | 7.11 | 11.50 |

The products according to the invention were studied for their therapeutic action. The interaction of the products according to the invention with muscarinic cholinergic receptors was determined in particular.

In mammals, there are two subclasses of muscarinic cholinergic receptors: the $M_1$ and $M_2$ receptors.

The $M_1$-type receptors are concentrated in certain areas of the brain, such as the hippocampus, the cerebral cortex and the striatum, and also in the sympathetic ganglia. These binding sites can be selectively labeled with [$^3$H]pirenzepine ([$^3$H]PZ). The $M_2$-type receptors predominate in the heart and ileum and can be labeled with [$^3$H]N-methylscopolamine ([$^3$H]NMS). To determine the selectivity of our molecules towards the $M_1$ and $M_2$ sites, we studied their interaction in vitro with [$^3$H]PZ and [$^3$H]NMS bound with a high affinity to membranes of rat hippocampus and membranes of smooth muscle of guinea-pig ileum, respectively.

METHODOLOGIES (A) Test for affinity for the Ml-type muscarinic cholinergic receptor The interaction of the molecules with $M_1$-type muscarinic receptors was studied by in vitro measurement, on a homogenate of rat hippocampus, of the displacement of tritiated pirenzepine ([$^3$H]PZ) from its specific binding sites. Aliquots (10 μl) of a 5% (w/v) homogenate of rat hippocampus in an $Na_2HPO_4$ buffer (50 mM, pH 7.40) are incubated for 2 h at 4° C. in the presence of [$^3$H]pZ (76 Ci/nmol; final concentration: 1 nM) and increasing concentrations of products to be studied. The final volume is 2 ml. The reaction is stopped by centrifugation for 10 min at 50,000 × g. After decantation and washing of the residues, the bound radioactivity is counted by liquid scintillation. The non-specific binding is determined in the presence of 10 μmol/l of atropine sulfate. The 50% inhibitory concentration (IC$_{50}$) is determined graphically (Ref.: Watson J. D., Roeskoe W. R. and Yamamura H.1., Life Sci., 31, 2019–2029, 1982).

(B) Test for affinity for the $M_2$-type muscarinic cholinergic receptor

The interaction with $M_2$-type muscarinic receptors was studied by in vitro measurement, on a homogenate of smooth muscle of guinea-pig ileum, of the displacement of tritiated N-methylscopolamine ([$^3$H]NMS) from its specific binding sites. Aliquots (50 μl) of a 0.625% (w/v) homogenate of smooth muscle of guinea-pig ileum in MEPES buffer (20 mM) containing NaCl (100 mM) and $MgCl_2$ (10 mM) (final pH: 7.5) are incubated for 20 min at 30° C. in the presence of [$^3$H]NMS (85 Ci/nmol; final concentration: 0.3 nM) and increasing concentrations of products to be tested. The final volume is 1 ml. The reaction is stopped by centrifugation for 5 min at 15,000 × g. The non-specific binding is determined in the presence of 10 μmol/l of atropine sulfate (Ref.: Hammer R., Berrie C. P., Birdsall N. I. M., Burgen A. S. V. and Hulme E. C., Nature, 283, 90–92, 1980; Hulme E. C., Birdsall N.l.M., Burgen A. S. V. and Mettha P., Mol. pharmacol., 14, 737–750, 1978).

RESULTS

Table 4 indicates the affinities of the products of the invention for $M_1$ and $M_2$ receptors. The results are expressed as 50% inhibitory concentrations ($IC_{50}$), i.e. the concentration (in μM) which causes a 50% displacement placement of the tritiated ligand bound to the membrane receptors. The $IC_{50}$ for displacement of $^3H$-pirenzepine represents the affinity for the $M_1$ receptor; the $IC_{50}$ for displacement of 3H-NMS represents the affinity for the $M_2$ receptor.

The table also indicates, in the 3rd column, the ratio r of the $M_1$ $IC_{50}$ values, which expresses the selectivity of the products towards one of the receptor types.

TABLE 4

| Product no. | $^3$H-Pirenzepine ($M_1$) $IC_{50}$ μM | $^3$H-NMS ($M_2$) $IC_{50}$ μM | r = ($M_2/M_1$) |
|---|---|---|---|
| SR 95695 A | 2.6 | 100 | 38 |
| SR 95679 A | 3.1 | 100 | 32 |
| SR 95746 A | 1.5 | 25 | 17 |
| SR 95743 A | 0.7 | 10 | 14 |
| SR 95745 A | 3.9 | 80 | 21 |
| SR 95639 A | 0.4 | 55 | 137 |
| SR 95640 A | 0.05 | 2 | 40 |
| SR 95776 A | 0.2 | 2 | 10 |
| SR 95777 A | 0.1 | 5.6 | 56 |
| SR 95818 A | 0.24 | 12 | 50 |
| SR 95820 A | 0.07 | 2 | 29 |
| SR 95822 A | 1 | 9.5 | 9.5 |
| SR 95824 A | 0.2 | 25 | 125 |
| SR 44694 A | 0.15 | 3.6 | 24 |
| SR 44695 A | 0.45 | 4.5 | 10 |
| SR 44664 A | 0.18 | 2 | 11 |
| SR 44696 A | 0.7 | 6.5 | 10 |
| SR 44705 A | 0.18 | 3 | 16 |
| SR 44706 A | 3.6 | 30 | 8 |
| SR 44703 A | 0.1 | 4 | 40 |
| SR 44681 A | 0.26 | 9 | 35 |
| SR 44697 A | 0.3 | 3 | 10 |
| SR 95776 A | 0.2 | 2 | 10 |
| SR 95746 A | 1.5 | 25 | 17 |
| SR 95695 A | 2.6 | >100 | >38 |
| SR 95679 A | 3.1 | >100 | >32 |
| SR 95745 A | 3.9 | 80 | 21 |
| SR 95878 A | 0.04 | 1.1 | 26 |
| SR 95879 A | 0.14 | 1 | 7 |
| SR 96093 A | 1.2 | 50 | 42 |
| SR 95883 A | 0.13 | 4.5 | 35 |
| SR 96100 A | 0.4 | 44 | 110 |
| SR 96054 A | 0.21 | 7.5 | 36 |
| SR 96055 A | 0.32 | 17 | 53 |
| SR 96057 A | 3 | 43 | 14 |
| SR 44663 A | 0.16 | 5 | 37 |
| SR 96108 A | 1 | 40 | 40 |

These results show that the compounds according to the invention have a strong affinity for muscarinic cholinergic receptors with a marked specificity for $M_1$-type central receptors.

Some of the compounds according to the invention were also subjected to a pharmacological study in vivo.

PHARMACOLOGICAL STUDY IN VIVO

Pirenzepine (PZ) is a specific antagonist of $M_1$ central muscarinic cholinergic receptors. The intrastriatal injection of PZ into mice induces rotational behavior. The antagonism of this behavior by the products according to the invention was studied.

The products according to the invention are injected intraperitoneally (i.p.) after solubilization in distilled water or suspension in a 5% solution of gum arabic. The control animals receive an injection of the pure solvent under the same conditions.

The animals used are female mice (Swiss, CD 1, Charles River, France) with a body weight of between 25 and 30 grams.

Pirenzepine is dissolved in a phosphate buffer; the pH of the solution is 6.

The products to be studied or their solvents are injected intraperitoneally, in a volume of 0.4 ml per 20 g of body weight, 15 minutes before a direct injection of pirenzepine at a dose of 1 μl of solvent into the right striatum of the mouse, according to the method described by p. WORMS et al. in Eur. J. Pharmacol., 1986, 121, 395–401.

The number of contralateral rotations (rotations in the opposite direction to the side injected) was counted for three 2-minute periods after the injection of pirenzepine: minutes 2 to 4, 8 to 10 and 13 to 15. Each treatment includes 3 to 4 doses and 10 animals per dose. For each treatment, the total number of rotations and the percentage antagonism compared with the control group are calculated.

The 50% effective dose ($ED_{50}$), i.e. the dose which causes a 50% reduction in the number of rotations induced by pirenzepine, is determined graphically for each product. The results are reported in Table 5.

TABLE 5

| Product no. | Pirenzepine antagonism $ED_{50}$ mg/kg i.p. |
|---|---|
| SR 95695 A | 5 |
| SR 95679 A | 10 |
| SR 95746 A | 10–30 |
| SR 95743 A | 8 |
| SR 95745 A | 8 |
| SR 95639 A | 5 |
| SR 95640 A | 3 |
| SR 95696 A | 3 |
| SR 95777 A | 0.5 |
| SR 95817 A | 2 |
| SR 95818 A | 7 |
| SR 95819 A | 10 |
| SR 95820 A | 8 |
| SR 95822 A | 3 |
| SR 95824 A | 3 |
| SR 44650 A | 3 |
| SR 44664 A | 3 |
| SR 44681 A | 1 |
| SR 96093 A | 15 |
| SR 96054 A | 3 |
| SR 96055 A | 3 |
| SR 44663 A | 1 |
| SR 95878 A | 2 |
| SR 95879 A | 0.3 |
| SR 95883 A | 3 |

Furthermore, tests carried out on some of the compounds according to the invention demonstrated that the compounds (I) pass through the blood-brain and digestive barriers.

Finally, the compounds according to the invention showed no signs of apparent toxicity at the doses at which they are active.

Consequently, the compounds (I) can be used as drugs, especially in cases where a cortical cholinergic deficit is evident and in particular in the case of dementia of the Alzheimer type.

According to another of its features, the present Application therefore relates to pharmaceutical compositions in which at least one of the compounds of the formula (I) or one of their salts is present as the active ingredient.

In the pharmaceutical compositions of the present invention for oral, sublingual, subcutaneous, intramuscular, intravenous, percutaneous or rectal administration, the active ingredients of the formula (I) above can be administered to humans in unit forms of administration, mixed with conventional pharmaceutical excipients, especially for the treatment of senile dementia. Appropriate unit forms of administration include forms for oral administration, such as tablets, gelatin capsules, powders, granules and oral solutions or suspensions, forms for sublingual and buccal administration, forms for subcutaneous, intramuscular or intravenous administration and forms for rectal administration.

To obtain the desired effect, the dose of active principle can vary between 50 and 2000 mg per day.

Each unit dose can contain from 10 to 500 mg of active ingredient in combination with a pharmaceutical excipient. This unit dose can be administered 1 to 4 times per day.

If a solid composition is prepared in the form of tablets, the main active ingredient is mixed with pharmaceutical vehicle such as gelatin, starch, lactose, magnesium stearate, talc, gum arabic or the like. The tablets can be coated with sucrose or other appropriate materials; alternatively, they can be treated so that they have a prolonged or delayed activity and so that they release a predetermined amount of active principle continuously.

A preparation in the form of gelatin capsules is obtained by mixing the active ingredient with a diluent and pouring the resulting mixture into soft or hard gelatin capsules.

Powders or granules which are dispersible in water can contain the active ingredient mixed with dispersing, wetting or suspending agents such as polyvinylpyrrolidone, as well as with sweeteners or taste correctors.

Rectal administration is effected using suppositories which are prepared with binders melting at the rectal temperature, for example cacao butter or polyethylene glycols.

Parenteral administration is effected using aqueous solutions, isotonic saline solutions or injectable sterile solutions which contain pharmacologically compatible dispersing and/or wetting agents, for example propylene glycol or butylene glycol The active principle can also be formulated as microcapsules, if appropriate with one or more excipients or additives.

Thus, by way of example, it is possible to prepare gelatin capsules based on one of the compounds of Examples 1 to 37 and having the following composition:

| Active principle | 25 mg |
|---|---|
| Lactose | 110 mg |
| Magnesium stearate | 5 mg | by intimately mixing the above ingredients and pouring the mixture into hard gelatin capsules.

What is claimed is:

1. A tricyclic pyridazine derivative having the formula:

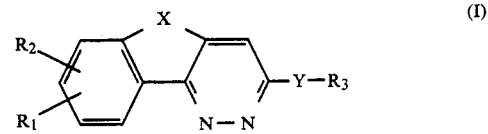

wherein:
X represents a group $(CH_2)_n$, where n is an integer equal to 2, 3 or 4, or alternatively a vinylene group or a methylvinylene group;

$R_1$ and $R_2$, each independently represent hydrogen or a substituent occupying one of the free positions of the benzene ring and selected from the group consisting of halogens, a lower alkyl group, a lower alkoxy group, a hydroxyl group, a thiol group, a nitro group, an amino group, a mono- or di-(lower) alkyl amino group and a mono- or di-(lower acyl amino group;

Y represents oxygen, sulphur or a group —NH—; and $R_3$ represents:

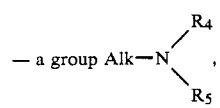

Alk represents a linear or branched alkylene group having from 2 to 5 carbon atoms; and $R_4$ and $R_5$ each independently represents hydrogen, a lower alkyl group or a lower hydroxyalkyl group, or alternatively $R_4$ and $R_5$ form, with the nitrogen atom to which they are bonded, an unsubstituted or lower alkyl-substituted pyrrolidin-1-yl, piperidino, morpholino, piperazin-1-yl or 2-oxomorpholino group;

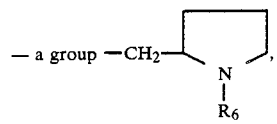

in which $R_6$ represents a lower alkyl group having 1 to 4 carbon atoms; or

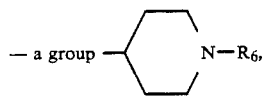

in which $R_6$ is as defined above;
and salts thereof with pharmaceutically acceptable mineral or organic acids.

2. A compound as claimed in claim 1 in which X represents a group $(CH_2)_n$ where n is equal to 2, 3 or 4.

3. A compound as claimed in claim 1 in which X represents a vinylene or methylvinylene group.

4. A compound according to claim 1, wherein $R_1$ and $R_2$ are each hydrogen.

5. A compound according to claim 1, wherein $R_1$ is an amino group and $R_2$ is hydrogen.

6. A compound according to claim 1, wherein Y represents NH.

7. A compound according to claim 1, wherein $R_1$ and $R_2$ each independently are $CH_3$ or $C_2H_5$.

8. A compound according to claim I, wherein Alk represents $(CH_2)_n$ where n is 2 or 3.

9. A compound according to claim 1, wherein $R_1$ and $R_2$ each independently are Cl or F.

10. A compound according to claim 1, wherein $R_4$ and $R_5$ each independently are $CH_3$ or $C_2H_5$.

11. A pharmaceutical composition, comprising an amount, effective to treat cholinergic deficit in a person suffering from senile dementia, of a tricyclic pyridazine derivative according to claim 1, in combination with a pharmaceutically acceptable vehicle.

12. A pharmacuetical composition according to claim 11, wherein X represents a group $(CH_2)_n$ where n is equal to 2, 3 or 4.

13. A pharmaceutical composition according to claim 11, wherein X represents a vinylene or methylvinylene group.

14. A pharmaceutical composition according to claim 11, wherein the group $R_3$ denotes

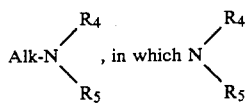

represents an unsubstituted or lower alkyl-substituted pyrrolidin-1-yl, piperidino, morpholino, piperazin-1-yl or 2-oxomorpholino group.

15. A pharmaceutical composition according to claim 11, wherein Y represents NH.

16. A pharmaceutical composition according to claim 11, wherein Alk represents $(CH_2)_n$ where n is equal to 2 or 3.

17. A pharmaceutical composition according to claim 11, wherein $R_1$ and $R_2$ each are hydrogen.

18. A pharmaceutical composition according to claim 11, wherein $R_1$ and $R_2$ each independently represents $CH_3$ or $C_2H_5$.

19. A pharmaceutical composition according to claim 11, wherein $R_4$ and $R_5$ each independently represents $CH_3$ or $C_2H_5$.

* * * * *